United States Patent [19]

Hagen et al.

[11] 4,261,924

[45] Apr. 14, 1981

[54] 4-NITRO-2-TRICHLOROMETHYLPHENYL-SULFENAMIDES

[75] Inventors: Helmut Hagen, Frankenthal; Ernst-Heinrich Pommer, Limburgerhof; Wolfgang Reuther, Heidelberg-Ziegelhausen; Hans Ziegler, Frankenthal, all of Fed. Rep. of Germany

[73] Assignee: BASF Aktiengesellschaft, Fed. Rep. of Germany

[21] Appl. No.: 78,724

[22] Filed: Sep. 25, 1979

[30] Foreign Application Priority Data

Oct. 6, 1978 [DE] Fed. Rep. of Germany ....... 2843644

[51] Int. Cl.$^3$ ...................... C07C 145/02; A01N 9/20
[52] U.S. Cl. .................................. 564/102; 424/248.5; 424/251; 424/267; 424/270; 424/269; 424/273 R; 424/274; 424/275; 424/304; 424/309; 424/317; 424/320; 424/330; 260/326.82; 260/326.9; 260/465 E; 544/106; 544/322; 546/264; 546/192; 548/146; 548/152; 548/255; 548/337; 560/17; 562/431; 260/239 B
[58] Field of Search ........ 260/551 S, 465 E, 448.2 N; 560/17; 562/431

[56] References Cited

U.S. PATENT DOCUMENTS

| 4,054,603 | 10/1977 | Beck et al. | 260/551 S |
|---|---|---|---|
| 4,163,020 | 7/1979 | Hagen et al. | 260/454 |

FOREIGN PATENT DOCUMENTS 2721917 11/1978 Fed. Rep. of Germany .

OTHER PUBLICATIONS

Moore et al., JACS 58, pp. 1960–1961, (1936).
Australian Abstract 62,679/60, Geigy A. G., (1961).
Baruffini et al., CA 61: 5550e, (1964).
Everitt et al., CA 34: 4107$^7$, (1940).
Chemical Week, Jun. 21, 1972, pp. 46, 63.

*Primary Examiner*—Thomas A. Waltz
*Attorney, Agent, or Firm*—Keil & Witherspoon

[57] ABSTRACT

New 4-nitro-2-trichloromethylphenylsulfenamides having a fungicidal and bactericidal action, processes for their manufacture, fungicides containing these compounds as active ingredients, and a process for combating fungi with these compounds.

3 Claims, No Drawings

4-NITRO-2-TRICHLOROMETHYLPHENYLSUL-FENAMIDES

The present invention relates to new and valuable 4-nitro-2-trichloromethylphenylsulfenamides having a fungicidal and bactericidal action, processes for their manufacture, fungicides containing these compounds as active ingredients, and a process for combating fungi with these compounds.

The use of N-trichloromethylthiophthalimide and N-trichloromethylthiotetrahydrophthalimide as fungicides has been disclosed (Chemical Week, June 21, 1972, pp. 46 and 63). However, their action is unsatisfactory.

The object of the present invention was therefore to provide new active ingredients having an improved fungicidal action.

We have found that 4-nitro-2-trichloromethylphenyl-sulfenamides of the formula

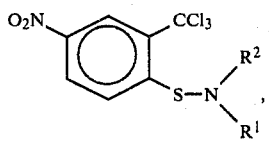

where $R^1$ and $R^2$ are identical or different and each denotes hydrogen, substituted or unsubstituted alkyl of from 1 to 18 carbon atoms, unsubstituted or substituted alkenyl of from 2 to 18 carbon atoms, unsubstituted or substituted alkynyl of from 3 to 5 carbon atoms, unsubstituted or substituted cycloalkyl of from 5 to 8 carbon atoms, an unsubstituted or substituted araliphatic radical of from 7 to 9 carbon atoms, an unsubstituted or substituted mono- or polynuclear aromatic radical, or a 5- to 7-membered methylene ring which may or may not contain from 1 to 3 nitrogen, oxygen or sulfur atoms as hetero atoms, or its benz homologs, or $R^1$ and $R^2$, together with the nitrogen atom whose substituents they are, denote a 5- to 7-membered saturated or unsaturated methylene ring which is substituted or unsubstituted and may or may not contain one or more nitrogen, oxygen or sulfur atoms as hetero atoms, or the benz homolog of the heterocyclic radical, and $R^1$ further denotes 4-nitro-2-trichloromethylphenylsulfenyl, have a better fungicidal and bactericidal action then the prior art active ingredients.

Examples of meanings for $R^1$ and $R^2$ are linear or branched alkyl of 1 to 18 carbon atoms optionally substituted by carboxyl, hydroxyl, nitrile, amino, keto, dialkylamino, trialkoxysilyl, alkoxy or carbalkoxy with 1 to 3 carbon atoms in the alkyl, e.g., methyl, ethyl, isopropyl, n-propyl, isobutyl, octyl, stearyl, n-dodecyl, methoxyethyl, hydroxyethyl, and triethoxysilylpropyl; cycloalkyl, e.g., cyclohexyl; linear or branched alkenyl of 2 to 18 carbon atoms or linear or branched alkynyl of 3 to 5 carbon atoms which may or may not be substituted by halogen, carboxyl or hydroxyl, e.g., allyl, methallyl, and propynyl; an araliphatic radical, for instance benzyl or phenylethyl, which is optionally substituted on the phenyl 1 to 3 times for example by halogen, nitro or cyano, e.g., chlorobenzyl, dichlorobenzyl, and nitrobenzyl, or an aromatic radical, for instance a benzene hydrocarbon optionally substituted 1 to 3 times, especially phenyl which may or may not be substituted by cyano, halogen, especially chlorine, nitro, or trifluoromethyl, e.g., dichlorophenyl, nitrophenyl, chloronitrophenyl, and chlorotrifluoromethylphenyl.

$R^1$ may further denote a heterocyclic radical, e.g., pyridyl, benzthiazolyl, pyrimidyl, or thiazolyl, which may or may not be substituted by halogen or phenyl in the heterocycle or by halogen, nitro or cyano in the benzene ring; where $R^1$ has this meaning, $R^2$ may denote hydrogen or alkyl.

Examples of heterocyclic radicals for $R^1$ and $R^2$ together with N are saturated or unsaturated heterocycles which may or may not contain, in addition to N, nitrogen, oxygen or sulfur atoms, e.g., the radical of morpholine, 3,5-dimethylmorpholine, pyrrolidine, pyrrole, piperidine, triazole, aminotriazole, hexahydroazepine or imidazole, which may or may not be substituted by methyl, ethyl, isopropyl, phenyl, nitro or halogen.

Preferred meanings of those given for $R^1$ and $R^2$ are hydrogen, alkyl of 1 to 12 carbon atoms optionally substituted by hydroxyl or halogen, alkenyl, alkynyl, phenyl or benzyl, optionally substituted by chlorine or alkyl, thiazole and benzthiazole, optionally substituted by chlorine, and pyridine or pyrimidine; preferred meanings for $R^1$ and $R^2$ together with N are imidazole optionally substituted by alkyl or phenyl, and morpholine optionally polysubstituted by alkyl.

The following list shows for instance preferred combinations of $R^1$ and $R^2$:

| $R^1$ | $R^2$ |
|---|---|
| H | H |
| ethyl | ethyl |
| isopropyl | H |
| n-propyl | H |
| n-octyl | H |
| cyclohexyl | H |
| cyclohexyl | methyl |
| p-nitrophenyl | H |
| benzyl | H |
| 2-thiazolyl | H |
| allyl | H |
| 2-hydroxyethyl | H |
| 2-pyridinyl | H |
| 2-chlorobenzyl | H |
| 2-benzthiazole | H |

Examples of preferred meanings for $R^1$ and $R^2$ together with N are:
imidazole
imidazole-2-phenyl
imidazole-2-methyl
imidazole-2-isopropyl
imidazole-4-nitro
imidazole-5-nitro
3,5-dimethylmorpholine The new compounds may be prepared by reaction of 4-nitro-2-trichloromethylbenzenesulfenyl chloride with a compound containing an amino group and in which $R^1$ and $R^2$ have the above meanings, in an inert solvent, at from $-40°$ to $+120°$ C., and in the presence of an agent which binds hydrogen chloride.

The reaction is illustrated by the following equation:

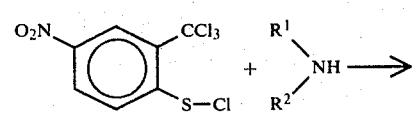

-continued

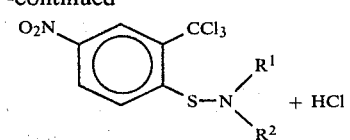 + HCl

Examples of suitable inert solvents for the reaction are saturated aliphatic or cyclic ethers, e.g., diethyl ether, diisopropyl ether, tetrahydrofuran and dioxane; anhydrous acetic acid; aliphatic carboxylic acid esters, e.g., ethyl acetate; and halogenated hydrocarbons, e.g., chloroform and methylene chloride. To bind the hydrogen chloride which is liberated, an excess of an amine of the formula $HNR^1R^2$ or, preferably, bases such as tertiary amines, e.g., triethylamine and pyridine, sodium or potassium acetate, or alkali metal carbonates, e.g., sodium carbonate, may be used.

The temperature range preferred for the reaction is from $-10°$ to $60°$ C.

The 4-nitro-2-trichloromethylbenzenesulfenyl chloride used as starting material may be manufactured for instance by chlorination of 5-nitrobenzo-1,2-dithio-3-thione in an inert solvent at from $-20°$ to $+100°$ C., preferably from $0°$ to $50°$ C. Examples of suitable inert solvents are chlorinated hydrocarbons, such as carbon tetrachloride, chloroform, dichloroethane, etc.

The reaction may be illustrated by the following equation:

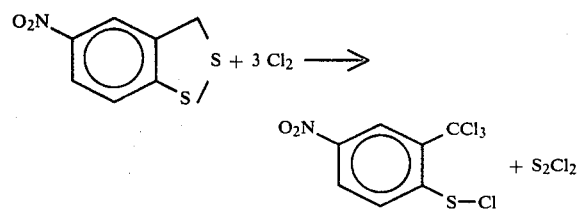

The 5-nitrobenzo-1,2-dithio-3-thione used as starting compound may be readily produced by the process described in German Laid-Open Application DE-OS No. 2,460,783, namely in the following manner.

51.5 g of 2-chloro-5-nitrobenzyl chloride is heated for 30 minutes at 50° C. with 24 g of sulfur in 500 ml of methanol. Over a period of 1 hour, 50.5 g of triethylamine is then added and the reaction mixture heated for 20 hours at 65° C. After the mixture has cooled, the precipitated solid is filtered and washed with water.

There is obtained 50.5 g (89% of theory) of 5-nitrobenzo-1,2-dithio-3-thione; m.p. 172°–173° C. (decomposes).

Manufacture of the compound

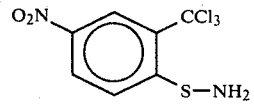

115 g of 5-nitrobenzo-1,2-dithio-3-thione is dispersed in 1,000 ml of carbon tetrachloride; at 10° C., 150 g of chlorine is passed in. The reaction mixture is stirred for 12 hours at room temperature (25 ° C.). The solvent and sulfur chloride are then distilled off under a water pump vacuum. 400 ml of diethyl ether is added to the residue and the mixture filtered. The ether solution is concentrated and distilled in vacuo. There is obtained 128 g (83% of theory) of 2-trichloromethyl-4-nitrobenzenesulfenyl chloride at 156°–160° C. (1 mm). The compound melts at 56°–57° C. (from ligroin).

The manufacture of the new compounds is illustrated in the following examples.

EXAMPLE 1

4-nitro-2-trichloromethylphenylsulfenamide

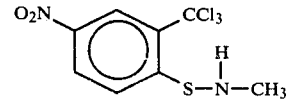

200 ml of a 20% strength (by weight) aqueous $NH_3$ solution is placed in a stirred apparatus; slowly and while stirring, a solution of 61.4 g of 4-nitro-2-trichloromethylbenzenesulfenyl chloride in 200 ml of diethyl ether is added at 20° C. After the mixture has been stirred for 1 hour at 20° C., the aqueous phase is separated, the ether phase is washed with water, and the ether is evaporated.

45 g (70% of theory) of 4-nitro-2-trichloromethylphenylsulfenamide (m.p.: 105° C.) is obtained from toluene.

| Analysis: | C | H | N | S | Cl | O |
|---|---|---|---|---|---|---|
| calc.: | 29.2 | 1.7 | 9.8 | 11.3 | 36.9 | 11.1 |
| found: | 29.2 | 1.7 | 9.7 | 11.2 | 37.0 | 11.2 |

EXAMPLE 2

N-methyl-4-nitro-2-trichloromethylphenylsulfenamide

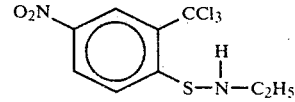

At 0° C., 10 liters of methylamine is passed into a solution of 61.4 g of 4-nitro-2-trichloromethylbenzenesulfenyl chloride in 200 ml of diethyl ether. After the mixture has been stirred for 6 hours at 25° C., it is poured onto ice water, and the aqueous phase is separated and evaporated to dryness. There is obtained 51 g (85% of theory) of N-methyl-4-nitro-2-trichloromethylphenylsulfenamide as an oil ($n_D^{20}$:1.6610).

| Analysis: | C | H | N | S | Cl | O |
|---|---|---|---|---|---|---|
| calc.: | 31.9 | 2.4 | 9.1 | 10.5 | 35.4 | 10.7 |
| found: | 31.8 | 2.3 | 9.3 | 10.6 | 35.3 | 10.6 |

EXAMPLE 3

N-ethyl-4-nitro-2-trichloromethylphenylsulfenamide

As in Example 1, 61.4 g of 4-nitro-2-trichloromethyl-benzenesulfenyl chloride is reacted with aqueous ethylamine solution.

There is obtained 56 g (90% of theory) of N-ethyl-4-nitro-2-trichloromethylphenylsulfenamide; m.p.: 80° C.

| Analysis: | C | H | N | S | Cl | O |
|---|---|---|---|---|---|---|
| calc.: | 34.2 | 3.1 | 9.0 | 9.9 | 33.7 | 10.2 |
| found: | 34.2 | 2.9 | 8.9 | 10.1 | 33.8 | 10.1 |

EXAMPLE 4

N,N-diisopropyl-4-nitro-2-trichloromethylphenylsulfenamide

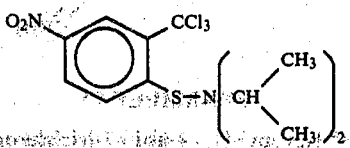

A solution of 40 g of diisopropylamine in 400 ml of ether is placed in a stirred apparatus; at 10° C., 61.4 g of 4-nitro-2-trichloromethylbenzenesulfenyl chloride in 200 ml of ether is dripped in. After the mixture has been reacted for 4 hours at 25° C., it is filtered and concentrated. There is obtained 70 g (95% of theory) of N,N-diisopropyl-4-nitro-2-trichloromethylphenylsulfenamide; m.p.: 104° C.

| Analysis: | C | H | N | S | Cl | O |
|---|---|---|---|---|---|---|
| calc.: | 41.9 | 4.6 | 7.6 | 8.8 | 28.7 | 8.4 |
| found: | 42.0 | 4.6 | 7.5 | 8.6 | 28.7 | 9.6 |

EXAMPLE 5

N,N-di-(2-methoxyethyl)-4-nitro-2-trichloromethylphenylsulfenamide

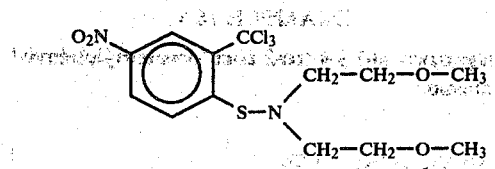

As in Example 4, 4-nitro-2-trichloromethylbenzenesulfenyl chloride is reacted with di-(2-methoxyethyl)-amine.

There is obtained 77 g (95% of theory) of N,N-di-(2-methoxyethyl)-4-nitro-2-trichloromethylphenylsulfenamide as a pale oil ($n_D^{20}$:1.6018).

| Analysis: | C | H | N | S | Cl | O |
|---|---|---|---|---|---|---|
| calc.: | 38.5 | 4.2 | 6.9 | 8.0 | 26.6 | 15.9 |
| found: | 38.7 | 4.2 | 6.9 | 7.9 | 26.4 | 15.9 |

EXAMPLE 6

N-(2-hydroxyethyl)-4-nitro-2-trichloromethylphenylsulfenamide

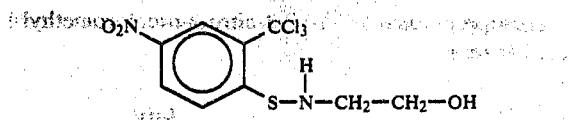

As in Example 4, 61.4 g of 4-nitro-2-trichloromethylbenzenesulfenyl chloride is reacted with 24 g of 2-aminoethanol.

There is obtained 60 g (90% of theory) of N-(2-hydroxyethyl)-4-nitro-2-trichloromethylphenylsulfenamide; m.p.: 85° C.

| Analysis: | C | H | N | S | Cl | O |
|---|---|---|---|---|---|---|
| calc.: | 32.4 | 2.5 | 8.3 | 9.9 | 32.2 | 14.6 |
| found: | 32.6 | 2.7 | 8.4 | 9.7 | 32.1 | 14.5 |

EXAMPLE 7

N-allyl-4-nitro-2-trichloromethylphenylsulfenamide

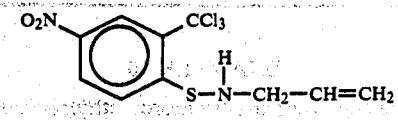

As in Example 4, 61.4 g of 4-nitro-2-trichloromethylbenzenesulfenyl chloride is reacted with 23 g of allylamine. The hydrochloride is filtered off and the ether phase is concentrated. There is obtained 62 g (95% of theory) of N-allyl-4-nitro-2-trichloromethylphenylsulfenamide as a pale oil.

| Analysis: | C | H | N | S | Cl | O |
|---|---|---|---|---|---|---|
| calc.: | 36.6 | 2.9 | 8.6 | 9.9 | 32.3 | 9.7 |
| found: | 36.6 | 2.7 | 8.5 | 9.8 | 32.5 | 9.8 |

EXAMPLE 8

(1,3-thiazol-2-yl)-4-nitro-2-trichloromethylphenylsulfenamide

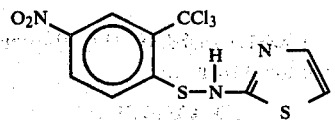

40 g of 2-aminothiazole is dissolved in 500 ml of tetrahydrofuran; while stirring and at 10° C., 61.4 g of 4-nitro-2-trichloromethylbenzenesulfenyl chloride is added. The addition of water precipitates the sulfenamide, which is filtered and recrystallized from ethyl acetate. There is obtained 50 g (70% of theory) of N-(1,3-thiazol-2-yl)-4-nitro-2-trichloromethylphenylsulfenamide; m.p.: 165° C.

| Analysis: | C | H | N | S | Cl | O |
|---|---|---|---|---|---|---|
| calc.: | 32.3 | 1.7 | 11.3 | 17.4 | 28.7 | 8.6 |
| found: | 32.4 | 1.6 | 11.3 | 17.3 | 28.7 | 8.6 |

EXAMPLE 9

(2-isopropylimidazol-1-yl)-4-nitro-2-trichloromethyl-thiobenzene

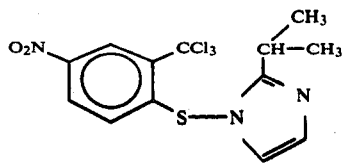

61.4 g of 4-nitro-2-trichloromethylbenzenesulfenyl chloride is reacted with 44 g of 2-isopropylimidazole in ether. After removal of the solvent and recrystallization from ether there is obtained 53 g (72% of theory) of (2-isopropylimidazol-1-yl)-4-nitro-2-trichloromethyl-thiobenzene as yellow crystals; m.p.: 135° C.

| Analysis: | C | H | N | S | Cl | O |
|---|---|---|---|---|---|---|
| calc.: | 41.4 | 3.2 | 11.1 | 8.2 | 27.9 | 8.4 |
| found: | 40.9 | 3.1 | 11.0 | 8.4 | 28.0 | 8.4 |

EXAMPLE 10

N,N-diethyl-(4-nitro-2-trichloromethylphenyl)-sulfenamide

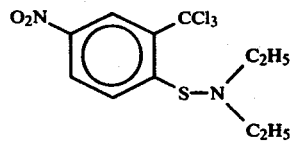

This compound is prepared in accordance with Example 4 from 4-nitro-2-trichloromethylbenzenesulfenyl chloride and diethylamine.

The yield is 65 g (95% of theory); m.p.: 60° C.

| Analysis: | C | H | N | S | Cl | O |
|---|---|---|---|---|---|---|
| calc.: | 38.3 | 3.7 | 8.4 | 9.3 | 31.1 | 9.2 |
| found: | 38.4 | 3.8 | 8.2 | 9.3 | 31.0 | 9.3 |

The compounds described in the following examples are obtained analogously.

EXAMPLE 11

(Morpholin-1-yl)-4-nitro-2-trichloromethylthiobenzene m.p.: 122° C.

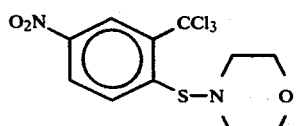

EXAMPLE 12

N,N-dimethyl-4-nitro-2-trichloromethylphenylsulfenamide

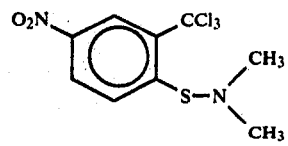
oil

EXAMPLE 13

N-(2-propyl)-4-nitro-2-trichloromethylphenylsulfenamide

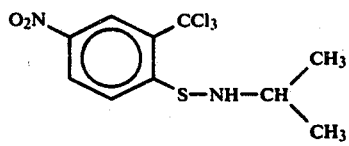
oil

EXAMPLE 14

N-(2-methylpropyl-(1))-4-nitro-2-trichloromethylphenylsulfenamide

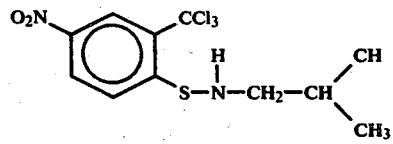
oil

EXAMPLE 15

N-(octyl-(1)-)-4-nitro-2-trichloromethylphenylsulfenamide

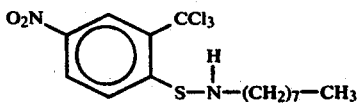
oil

EXAMPLE 16

N-(n-propyl-(1)-)-4-nitro-2-trichloromethylphenylsulfenamide

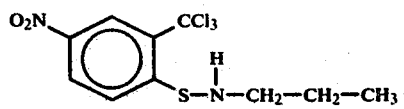
oil

EXAMPLE 17

N,N-(diallyl)-4-nitro-2-trichloromethylphenylsulfenamide

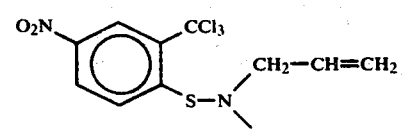
oil

EXAMPLE 18

N-(benzyl)-4-nitro-2-trichloromethylphenylsulfenamide oil

EXAMPLE 19

N-methyl-N-benzyl-4-nitro-2-trichloromethylphenylsulfenamide oil

EXAMPLE 20

N-(4-chlorobenzyl)-4-nitro-2-trichloromethylphenylsulfenamide oil

EXAMPLE 21

N-(2-chlorobenzyl)-4-nitro-2-trichloromethylphenylsulfenamide oil

EXAMPLE 22

N-ethyl-N-methallyl-(4-nitro-2-trichloromethylphenyl)-sulfenamide oil

EXAMPLE 23

N-stearyl-(4-nitro-2-trichloromethylphenyl)-sulfenamide oil

EXAMPLE 24

N-(2-hydroxyethyl-(1)-)-4-nitro-2-trichloromethylphenyulsulfenamide m.p.: 85° C.

EXAMPLE 25

N-cyclohexyl-(4-nitro-2-trichloromethylphenyl)-sulfenamide m.p.: 77° C.

EXAMPLE 26

N-phenyl-(4-nitro-2-trichloromethylphenyl)-sulfenamide m.p.: 139° C.

EXAMPLE 27

N-(4-toluyl)-4-nitro-2-trichloromethylphenylsulfenamide m.p.: 136° C.

EXAMPLE 28

N-(2,5-dichlorophenyl)-4-nitro-2-trichloromethylphenylsulfenamide m.p.: 139° C.

EXAMPLE 29

N-(3,5-dichlorophenyl)-4-nitro-2-trichloromethylphenylsulfenamide

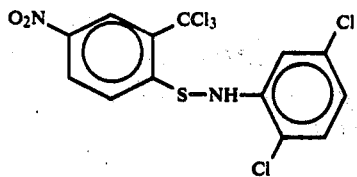

oil

EXAMPLE 30

N-(3,4-dichlorophenyl)-4-nitro-2-trichloromethylphenylsulfenamide

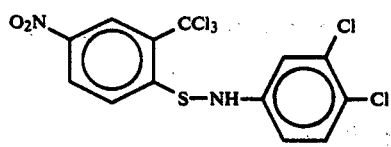

oil

EXAMPLE 31

N-(4-nitrophenyl)-4-nitro-2-trichloromethylphenylsulfenamide

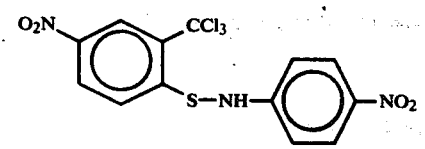

oil

EXAMPLE 32

N-phenyl-bis-(4-nitro-2-trichloromethylphenyl)-sulfenylamine

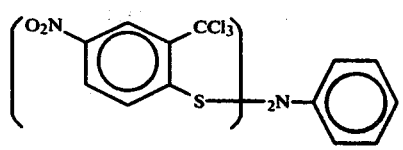

oil

EXAMPLE 33

(Pyrrolidin-1-yl)-4-nitro-2-trichloromethylthiobenzene

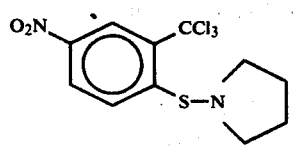

m.p.: 130° C.

EXAMPLE 34

(Piperidin-1-yl)-4-nitro-2-trichloromethylthiobenzene

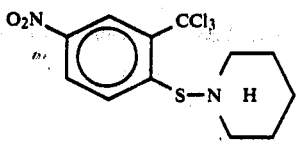

m.p.: 112° C.

EXAMPLE 35

(3,5-dimethylmorpholin-1-yl)-4-nitro-2-trichloromethylthiobenzene

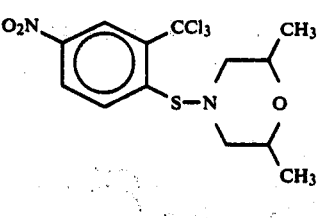

m.p.: 87° C.

EXAMPLE 36

(Hexahydroazepin-1-yl)-4-nitro-2-trichloromethylthiobenzene

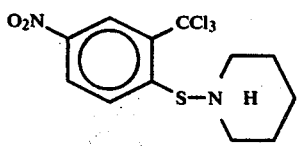

m.p.: 90° C.

EXAMPLE 37

N-(pyridin-2-yl)-4-nitro-2-trichloromethylphenylsulfenamide

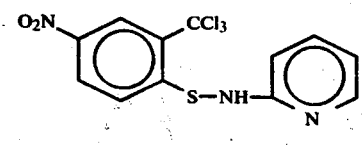

m.p.: 200° C.

EXAMPLE 38

(2-ethylimidazol-1-yl)-4-nitro-2-trichloromethylthiobenzene

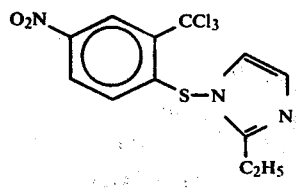

m.p.: 112° C.

EXAMPLE 39

(2-methylimidazol-1-yl)-4-nitro-2-trichloromethylthiobenzene

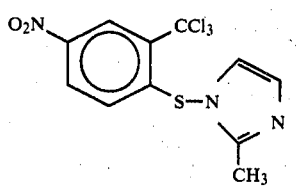

m.p.: 90° C.

EXAMPLE 40

(2-phenylimidazol-1-yl)-4-nitro-2-trichloromethylthiobenzene

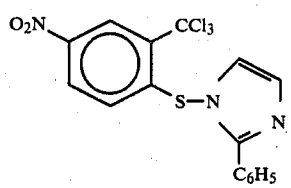

m.p.: 164° C.

EXAMPLE 41

N-ethyl-N-(3-chlorophenyl)-4-nitro-2-trichloromethylphenylsulfenamide

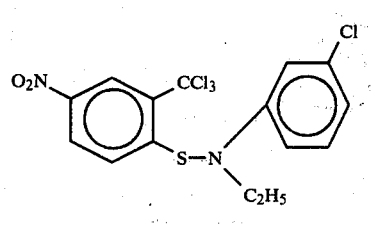

oil

EXAMPLE 42

N-(1,3-benzthiazol-2-yl)-4-nitro-2-trichloromethylphenylsulfenamide

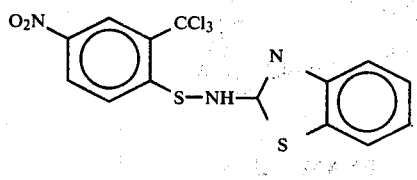

m.p.: 240° C.

EXAMPLE 43

N-(3-trifluoromethylphenyl)-4-nitro-2-trichloromethylphenylsulfenamide

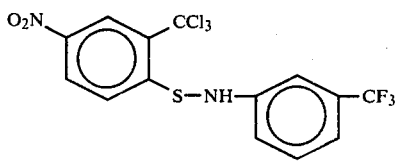

m.p.: 120° C.

EXAMPLE 44

N-(5-trifluoromethyl-2-chlorophenyl)-4-nitro-2-trichloromethylphenylsulfenamide

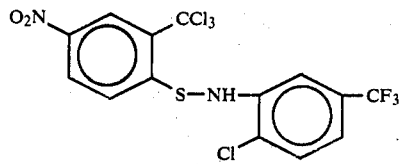

m.p. 112° C.

EXAMPLE 45

(Pyrrol-1-yl)-4-nitro-2-trichloromethylthiobenzene

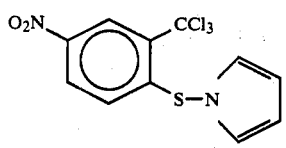

m.p.: 155° C.

EXAMPLE 46

N-(3-triethoxysilylpropyl)-4-nitro-2-trichloromethylphenylsulfenamide

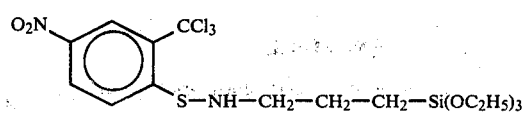

oil

EXAMPLE 47

N-cyclohexyl-N-methyl-4-nitro-2-trichloromethylphenylsulfenamide

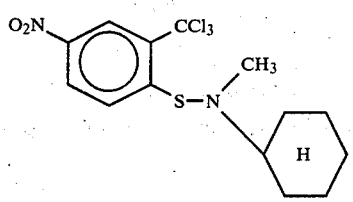

oil

EXAMPLE 48

(Imidazol-1-yl)-4-nitro-2-trichloromethylthiobenzene

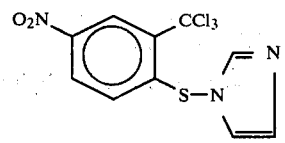

oil

EXAMPLE 49

(1,2-benzthiazol-3-yl)-4-nitro-2-trichloromethylphenylsulfenamide

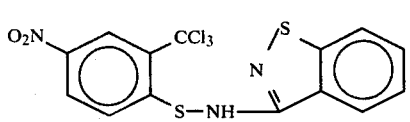

oil

EXAMPLE 50

[4(5)-nitroimidazol-1-yl]-4-nitro-2-trichloromethyl-thiobenzene

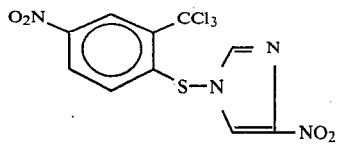

m.p.: 199° C.

The new compounds have a very good fungitoxic action on various kinds of injurious fungi which cause damage of economic significance to crops and materials, especially phytopathogenic fungi from the Phycomycetes class, e.g., *Plasmopara viticola* in grapes, *Pseudoperonospora humyli* in hops, *Septoria nodorum* in wheat, and *Peronospora tabacina* in tobacco. Examples of fungi from other classes which damage materials are *Aspergillus niger, Penicillium glaucum, Chaetomium globosum, Coniophora puteana* and *Serpula lacrimans*. The fungicidal agents contain from 0.1 to 95, and preferably from 0.5 to 90, wt% of active ingredient. Application rates depend on the desired effect, and range from 0.001 to 3 kg and more, but preferably from 0.01 to 1 kg of active ingredient per hectare. Where the active ingredients are used to protect materials, e.g., as fungicides for paints, application rates are from 0.5 to 5% of active ingredient, based on the total weight of the materials to be preserved (e.g., paints). The new active ingredients may also be used as fungicidally active components of oily wood preservatives for the protection of wood against wood-destroying or wood-discoloring fungi. The wood is treated with these agents for instance by impregnation or coating.

Some of the new compounds also have a good bactericidal action.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol glycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The active ingredients may also be mixed with other, prior art, fungicides. In many cases, the spectrum of fungicidal action is broadened; with a number of these fungicide mixtures synergistic effects also occur, i.e., the fungicidal action of the mixture is greater than the sum of the action of its individual components.

The following list of fungicides with which the compounds according to the invention can be combined is intended to illustrate possible combinations, but the invention is in no way limited to these. Examples of fungicides with which the 4-nitro-2-trichloromethyl-phenylsulfenamides according to the invention may be combined are as follows:
ferric dimethyldithiocarbamate
zinc dimethyldithiocarbamate
manganese ethylenebisdithiocarbamate
zinc ethylenebisthiocarbamate
tetramethylthiuram disulfide
3,5-dimethyl-1,3,5-2H-tetrahydrothiadiazine-2-thione
manganese-zinc ethylenediamine-bisdithiocarbamate
zinc-(,N,N'-propylene-bisdithiocarbamate)
ammonia complex of zinc-(N,N'-ethylene)-bisdithiocarbamate
and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
dinitro-(1-methylheptyl)-phenylcrotonate
2-sec-butyl-4,6-dinitrophenyl-3,5-dimethylacrylate 2-sec-butyl-4,6-dinitrophenylisopropylcarbonate
2,4,5-trichlorophenol
pentachlorophenol
barium salt of pentachlorophenol
pentachlorophenyl acetate
pentachlorobenzyl alcohol
di-(5-chloro-2-hydroxyphenyl)-methane
phenyl-(5-chloro-2-hydroxyphenyl)-methane
N-trichloromethylthiotetrahydrophthalimide
N-trichloromethylthiophthalimide
N-fluorodichloromethylthiophthalimide
N-(1,1,2,2-tetrachloroethylthio)-tetrahydrophthalimide
2-heptadecyl-2-imidazoline acetate
2,4-dichloro-6-(o-chloroanilino)-s-triazine
diethylphthalimidophosphorothioate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
quinoxaline-2,3-cycl.-trithiocarbonate
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
1-(1,2,4-triazolyl-1')-[4'-chlorophenoxy)]-3,3-dimethyl-butan-2-one
1-(1-imidazoyl)-2-allyloxy-2-(2,4-dichlorophenyl)-ethane
2-(O,O-diethylthionophosphoryl)-5-methyl-6-carbethoxypyrazolo-(1,5a)-pyrimidine
pyridine-2-thiol-1-oxide
8-hydroxyquinoline and its copper salt
5,5-dimethyl-3-(3,5-dichlorophenyl)-2,4-dioxo-1,3-oxazolidine
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
dodecylguanidine acetate
3-[2-(3,5-dimethyl-2-oxycyclohexyl)-2-hydroxyethyl]-glutarimide
hexachlorobenzene
N-dichlorofluoromethylthio-N,N'-dimethyl-N-phenyl-sulfuric acid diamide
N-dichlorofluoromethylthio-N-methyl-N'-methyl-N-phenylsulfuric acid diamide
2,4,5,6-tetrachloroisophthalonitrile
1-(3,4-dichloroanilino)-1-formylamino-2,2,2-trichloroethane
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzene diazosodium sulfonate
1-chloro-2-nitropropane
polychloronitrobenzenes such as pentachloronitrobenzene
methyl isothiocyanate
triphenyl tin acetate
fungicidal antibiotics, e.g., griseofulvin and kasugamycin
mercaptobenzothiazole
methyl-N-(2,6-dimethylphenyl)-N-(2-furoyl)-alaninate
methyl-N-(2,6-dimethylphenyl)-N-(2-methoxyacetyl)-alaninate
2-cyano-N-[(ethylamino)-carbonyl]-2-(methoximino)-acetamide
β-(4-chlorophenxy)-α-(1,1-dimethyl)-1H-1,2,4-triazole-1-ethanol
benzisothiazolone
tetrafluorodichloroacetone
1-phenylthiosemicarbazide
aluminum complex of N'-hydroxy-N-cyclohexyl-diazenium oxide
Bordeaux mixture
nickel-containing compounds, and sulfur.

These agents may be added to the fungicides according to the invention in a weight ratio of from 1:10 to 10:1. If desired, they need not be added until immediately before use (tankmix).

EXAMPLE 51

Fungicidal action on *Aspergillus niger*

The active ingredients are added to a nutrient solution ideally suited for promoting the growth of the fungus *Aspergillus niger*, in amounts of 100, 50, 25 and 10 parts by weight per million parts of nutrient solution. 20 ml lots of the nutrient solution treated in this manner are placed in 100 ml glass flasks and inoculated with 0.3 mg of Aspergillus spores. The flasks are incubated at 36° C. for 120 hours, and the extent of fungus spread—predominantly on the surface of the nutrient solutions—is then assessed.

0 = no fungus growth, graduated down to
5 = uncontrolled fungus growth (surface of nutrient solution) completely covered by fungus)

| Active ingredient from Ex. no. | Amount of active ingredient in ppm of nutrient solution | | | |
|---|---|---|---|---|
| | 100 | 50 | 25 | 10 |
| 2 | 0 | 0 | 3 | 4 |
| 6 | 0 | 0 | 2 | 4 |
| 9 | 0 | 0 | 0 | 2 |
| 10 | 0 | 0 | 2 | 2 |
| 11 | 0 | 0 | 0 | 2 |
| 12 | 0 | 0 | 0 | 3 |
| 15 | 0 | 0 | 0 | 2 |
| 16 | 0 | 0 | 0 | 3 |
| 18 | 0 | 0 | 0 | 2 |
| 20 | 0 | 0 | 2 | 3 |
| 40 | 0 | 0 | 2 | 4 |
| 47 | 0 | 0 | 2 | 2 |
| 49 | 0 | 2 | 2 | 3 |
| Comparative agent 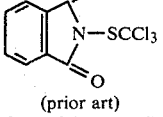 (prior art) | 1 | 1 | 3 | 4 |
| Control (untreated) | 5 | | | |

EXAMPLE 52

Fungicidal action on *Plasmopara viticola* in grapes

Leaves of pottes vines of the Müller-Thurgau variety are sprayed with aqueous suspensions containing (dry basis) 80% (wt%) of the active ingredient and 20% of sodium lignin sulfonate. 0.05 and 0.25% (dry basis) spray liquors are used. After the sprayed-on liquor has dried, the leaves are infected with a zoospore suspension of *Plasmopara viticola*. The plants are first placed for 16 hours in a steam-saturated (moist) chamber at 20° C., and then in a greenhouse for 8 days at from 20° to 30° C. To accelerate and intensify the sporangiophore discharge, the plants are then again placed in the moist chamber for 16 hours. Leaf attack is then assessed on the undersides of the leaves. Untreated infected plants were used as control.

| Active ingredient from Ex. no. | Leaf attack after spraying with liquor containing active ingredients in amounts of | |
|---|---|---|
| | 0.05% | 0.025% |
| 8 | 0 | 0 |
| 12 | 0 | 2 |
| 15 | 0 | 0 |
| 16 | 0 | 0 |
| 18 | 0 | 2 |
| 27 | 0 | 0 |
| 39 | 0 | 0 |
| Comparative agent 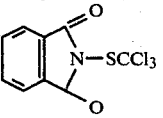 (prior art) | 2 | 3 |
| Control (untreated) | 5 | |

0 = no attack, graduated down to 5 = total attack

EXAMPLE 53

Bactericidal action on *Staphylococcus aureaus*

*Staphylococcus aureus* kill values were determined as follows. 5 ml of a 1:5,000 dilution of the active ingredients in water was placed in sterile test tubes and 5 ml of a doubly concentrated nutrient was admixed. The tubes were inoculated by adding one drop of 16-hour-old broth cultures (diluted 1:10 with water) of the bacteria species *Staphylococcus aureas;* the tubes were then incubated for 24 hours at 37° C. Samples from the tubes were then transferred to bacteria culture media which were in turn incubated for 24 hours at 37° C. No bacterial growth occurred after transfer to the culture media in the case of active ingredients nos. 6, 10, 12, 16, 18 and 26.

EXAMPLE 54

90 parts by weight of compound 1 is mixed with 10 parts by weight of N-methyl-α-pyrrolidone. A mixture is obtained which is suitable for application in the form of very fine drops.

EXAMPLE 55

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 56

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 57

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 58

20 parts by weight of compound 3 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 59

3 parts by weight of compound 3 is intimately mixed with 97 parts by weight of particulate kaolin. A dust is obtained containing 3% by weight of the active ingredient.

EXAMPLE 60

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 61

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 62

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:
1. A 4-nitro-2-trichloromethylphenylsulfenamide of the formula

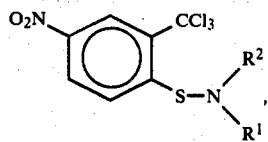

where $R^1$ and $R^2$ are identical or different and each denotes hydrogen, substituted or unsubstituted alkyl of from 1 to 18 carbon atoms, unsubstituted or substituted alkenyl of from 2 to 18 carbon atoms, unsubstituted or substituted alkynyl of from 3 to 5 carbon atoms, unsubstituted or substituted cycloalkyl of from 5 to 8 carbon atoms, an unsubstituted or substituted araliphatic radical of from 7 to 9 carbon atoms, or an unsubstituted or substituted mono- or polynuclear aromatic radical, and $R^1$ further denotes 4-nitro-2-trichloromethylphenylsulfenyl.

2. A 4-nitro-2-trichloromethylphenylsulfenamide selected from the group consisting of N-(octyl-(1))-4-nitro-2-trichloromethylphenylsulfenamide and N-(n-propyl-(1))-4-nitro-2-trichloromethylphenylsulfenamide.

3. A 4-nitro-2-trichloromethylphenylsulfenamide as set forth in claim 1 wherein $R^1$ and $R^2$ are both ethyl.

* * * * *